United States Patent [19]

Weissman

[11] 4,393,539
[45] Jul. 19, 1983

[54] OVERHANDLE FOR ENCLOSING A DENTAL TOOL HANDLE OR SHANK

[75] Inventor: Bernard Weissman, New York, N.Y.

[73] Assignee: Ipco Corporation, White Plains, N.Y.

[21] Appl. No.: 214,664

[22] Filed: Dec. 9, 1980

[51] Int. Cl.³ .............................................. B25G 3/38
[52] U.S. Cl. ........................... 16/114 R; 16/DIG. 18;
16/DIG. 24; 30/340; 81/177 R; 145/61 R;
433/147; 433/225
[58] Field of Search ............. 16/110 R, 111 R, 111 A,
16/112, 114 R, DIG. 12, DIG. 18, DIG. 19,
DIG. 24, DIG. 25; 145/61 R, 61 C, 61 K;
81/177 R, 177 A; 408/241 R; 30/340; 74/551.9;
433/102, 126, 127, 141, 147, 225

[56] References Cited

U.S. PATENT DOCUMENTS

| 604,706 | 5/1898 | Wiens et al. | 74/551.9 |
| 2,102,839 | 12/1937 | Dohrman | 145/61 R |
| 3,072,955 | 1/1963 | Mitchell | 16/114 R X |
| 3,520,059 | 7/1970 | Gringer | 30/340 X |
| 3,672,054 | 6/1972 | Kaufman | 30/294 |

Primary Examiner—Fred Silverberg
Attorney, Agent, or Firm—Goodman & Teitelbaum

[57] ABSTRACT

An overhandle for enclosing the handle or the shank of a tool, such as a dental tool. The overhandle is formed of two mating semi-cylindrical sections having respective forward end faces which are confrontingly opposed in the opened condition and are in a single plane in the assembled closed condition. Laterally spaced apart hinges interlock the sections at their forward end faces. An elongated channel is respectively formed in each of the sections and extends through the forward end face of the respective section. The channels matingly confront in the assembled closed condition to define an internal chamber with an open forward end so that the chamber receives the end of the tool with the remaining tool portion axially extending through the open forward end. A coupling mechanism is provided for retaining the sections in the assembled closed condition. In modified embodiments, the same overhandle can enclose either the handle of one tool or the shank of another tool.

15 Claims, 12 Drawing Figures

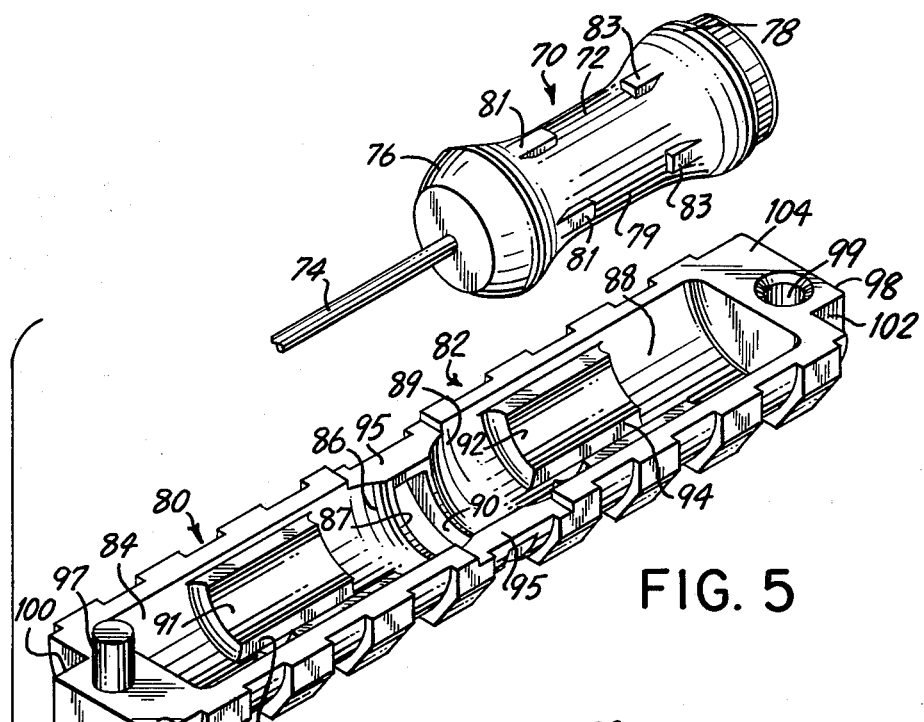
FIG. 5
FIG. 6
FIG. 7
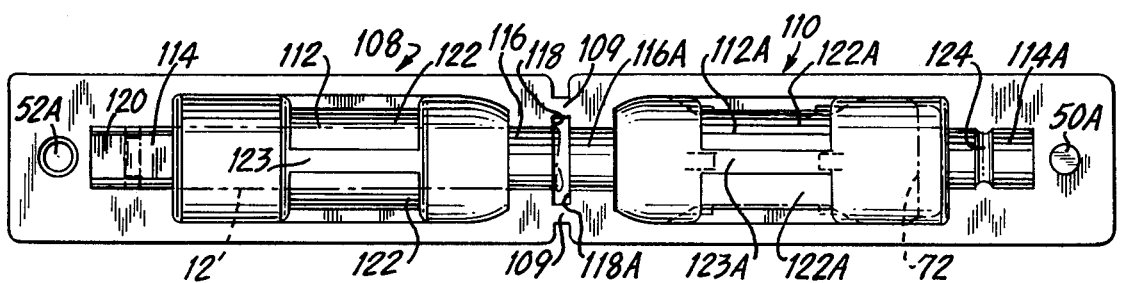
FIG. 8

OVERHANDLE FOR ENCLOSING A DENTAL TOOL HANDLE OR SHANK

BACKGROUND OF THE INVENTION

This invention relates generally to tools, and particularly to an overhandle for enclosing the existing handle or shank of a tool, such as a dental tool.

Tools, blades, such as drills, reamers, punches, etc., are usually held by means of a handle. With manually held tools, the tool blade is usually embedded permanently into the handle and the handle is of a size that it can be manipulated by the operator. With machine driven tools, the tool blade is usually held by its shank portion which in turn is retained within motor drive equipment.

In connection with the hand held manually operated tool, the handle may frequently be rather small, such as of a type held between the fingers of the user. The user may often require a larger size handle, however, the manufacturers normally provide for only a single size handle and accordingly, the user may be forced to utilize the smaller handle and thereby be inconvenienced.

Similarly, although a tool blade may be held by its shank for operation by an automatic machine, the user may desire to convert the engine driven tool into a hand operated tool. However, for such purposes he would need a grasping handle to hold onto the shank portion in order to grip the tool and be able to manipulate it.

It would therefore be desirous to have some sort of an overhandle which could be utilized to enclose the handle of a hand held tool in order to enlarge the handle size to thereby facilitate manipulation thereof by the user. It would also be desirous to provide an overhandle which can enclose the shank portion to an engine driven tool in order to convert the tool to a hand operated tool. It would still further be desirous to have a single type of overhandle which could be utilized both in conjunction with a hand operated tool for enlarging the handle portion, as well as for use with an engine driven tool to convert it into a hand held tool.

These particular objectives would especially be desirous in the field of dentistry where the size of the tools are generally small. In connection with various aspects of dentistry, such as particularly in connection with root canal work, the dentist utilizes small tools for carrying out the root canal work. Such tools include drill bits, reamers, pins, etc. Usually, such tools have very small handles which are manipulated between the dentist's fingers, as for example rotating the tool between the index finger and the thumb of the dentist.

For many dentists, the size of the handle may be too small, whereby he may desire a larger handle for a particular operation. At the same time, though the dentist may have many types of engine driven tools, the particular size drill that he would desire to use as a hand operated tool for root canal work may only be stocked by him as an engine driven tool. Therefore, the dentist is required to stock a complete set of engine driven tools as well as a complete set of hand operated tools.

SUMMARY OF THE INVENTION

It is accordingly an object of the present invention to provide an overhandle for enclosing the existing handle or shank of a tool.

It is a further object of the present invention to provide an overhandle for enclosing the existing handle of a hand operated tool in order to enlarge the size of the handle.

Still a further object of the present invention is to provide an overhandle for enclosing the shank portion of an engine driven tool in order to convert it to a hand operated tool.

Still a further object of the present invention is to provide on overhandle for enclosing either the existing handle of a hand operated tool or the shank portion of an engine driven tool.

A further object of the present invention is to provide an overhandle for enclosing the existing handle or shank of a tool, which overhandle is formed of a single piece of material and can be assembled to enclose the existing handle or shank of the tool.

Still another object of the present invention is to provide an overhandle for enclosing the existing handle or shank of a tool which can be easily mounted and removed from the tool.

Yet a further object of the present invention is to provide an overhandle for enclosing the existing handle or shank of a tool formed of two mating sections which can be folded over the existing handle or shank of the tool and locked into an assembled condition.

Briefly, in accordance with the present invention, there is provided an overhandle for enclosing the existing handle or shank of a tool. The overhandle is formed of two mating semi-cylindrical sections having forward end faces which are confrontingly opposed in the opened condition and are in a single plane in the assembled closed condition. Laterally spaced apart hinges interconnect the sections at their forward end faces. An elongated recess is respectively formed in each of these sections and extends through the respective forward end face of each section. The recesses matingly confront with each other in the assembled closed condition to define an internal chamber with an open forward end. The internal chamber receives the existing handle or shank of the tool with the remaining portion of the tool, such as the blade, axially extending through the open forward end of the overhandle. A coupling mechanism is provided for retaining the two sections in their assembled closed condition.

BRIEF DESCRIPTION OF THE DRAWINGS

With the above and additional objects and advantages in view, as will hereinafter appear, this invention comprises the devices, combinations and arrangements of parts hereinafter described by way of example and illustrated in the accompanying drawings of a preferred embodiment in which:

FIG. 5 is an exploded perspective view of an overhandle in accordance with a second embodiment of the present invention in its opened condition for receiving a hand operated tool;

FIG. 6 is a side sectional view of the overhandle of FIG. 5 in an assembled closed condition enclosing the hand operated tool;

FIG. 7 is a fragmentary perspective end view showing the rear end of the overhandle of FIG. 6;

FIG. 8 is a plan view of an overhandle in an opened condition in accordance with a third embodiment of the present invention, including the capabilities of the first two embodiments;

In the various figures of the drawing like reference characters designate like parts.

DETAILED DESCRIPTION OF THE PREFERRED EMBODIMENT

Figure 1:
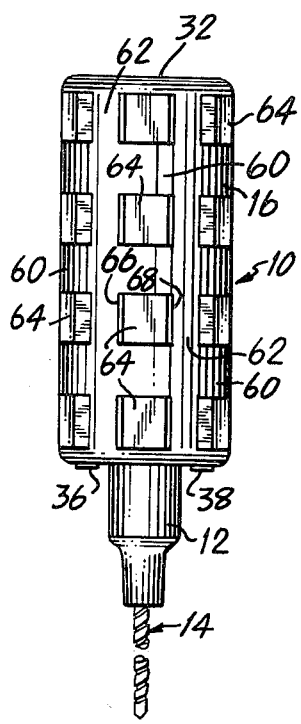
FIG. 1 is a side view of an overhandle of the present invention, showing it enclosing the shank portion of an engine driven tool.

Referring now to FIGS. 1-4, a first embodiment of the overhandle of the present invention will be described. Such overhandle is shown generally at 10 and is used for receiving the shank portion 12 of a tool, the tool specifically being shown in FIG. 1 as a dental drill bit 14. It should be understood, however, that numerous other types of tools can be utilized such as dental anchors, reamers, etc.

The overhandle 10 is formed of two mating semi-cylindrical sections 16, 18. Section 16 includes a semi-cylindrical outer surface 20 and a substantially flat upper surface 22 interconnected by the rear end face 24 and the forward end face 26. Similarly, section 18 includes a semi-cylindrical outer surface 28, a substantially flat upper surface 30, a rear end face 32, and a forward end face 34.

Figure 3:
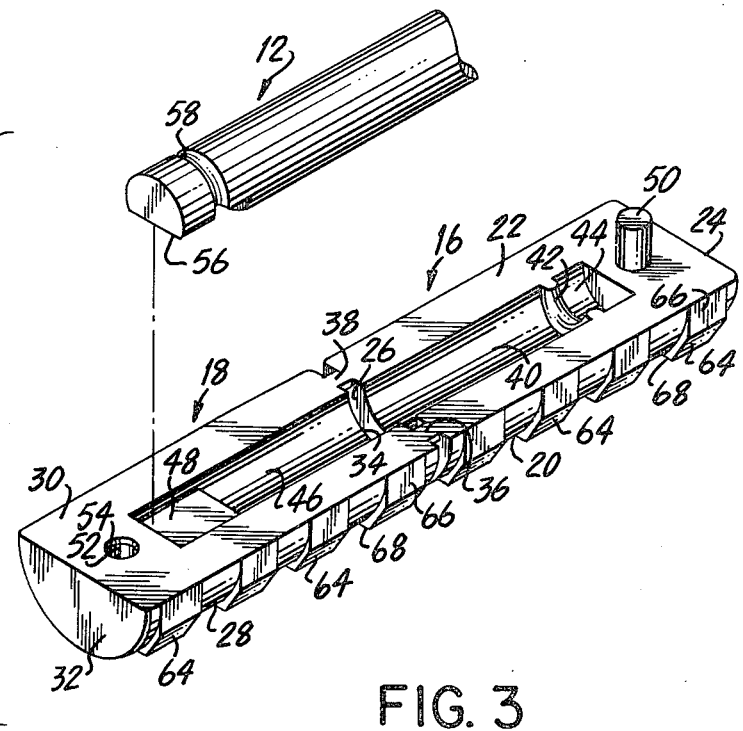
FIG. 3 is an exploded perspective view showing the overhandle of the present invention in its opened condition to receive the shank portion of an engine driven tool.
Figure 4:
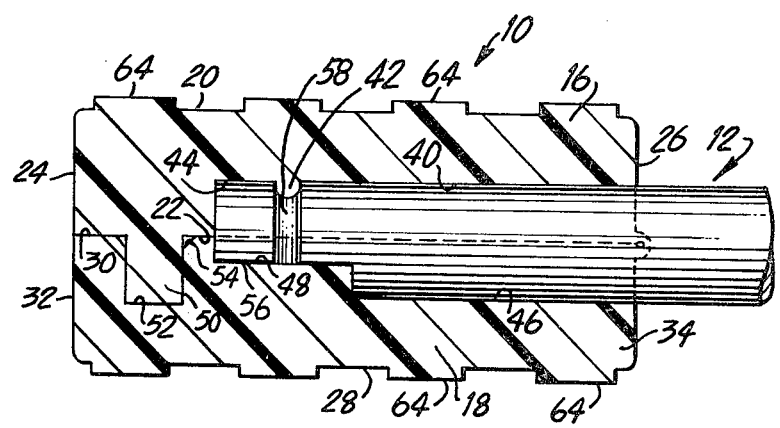
FIG. 4 is a cross-sectional side view showing the overhandle in an assembled closed condition enclosing the shank portion of an engine drive tool.

The forward end faces 26, 34 are confrontingly opposed in the opened condition, as shown in FIG. 3, and are in a single common plane in the assembled closed condition, as shown in FIG. 4. Likewise, the flat upper faces 22, 30 lie in a common plane in the opened condition, as shown in FIG. 3, and confrontingly opposed each other in the assembled closed condition, as shown in FIG. 4. The two sections 16, 18, are secured together by means of the laterally spaced apart hinges 36, 38 which lie in the common plane of the upper surfaces 22, 30 and interconnect the sections 16, 18 at their confronting forward end faces 26, 34. The hinges are shown formed integral with the sections and the overhandle 10 can be formed out of a plastic or nylon material in a single molding process, or the like. The hinges 36, 38 are shown as being narrowed sections as compared with the width of the flat sections 22, 30 to which they are interconnected.

Section 16 includes a substantially semi-cylindrical channel or recess 40 which extends through the forward end face 26 and terminates within its opposite end in spaced relationship to the rear end face 24. A circumferential rib 42 is formed adjacent the rear end of the channel 40 in order to define a smaller recess 44 therein.

A corresponding channel or recess 46 of substantially similar semi-cylindrical shape is formed in the section 18 and extends through the forward end face 34 with the other end terminating in spaced relationship from the rear end face 32. A seat 48 is formed at the rear section of the channel 46. The channels 40, 46 are of equal length, as indicated in FIG. 4, so as to match each other in the closed condition to provide an inner chamber for accommodating the shank portion 12.

The two sections 16, 18 are held together by means of a locking arrangement including an upwardly extending locking pin 50 provided on a rear portion of the upper flat surface 22 of the section 16, and a downwardly extending socket 52 provided in a rear portion of the upper flat surface 30 of the section 18. The locking pin 50 and the socket 52 are properly spaced apart in the opened condition so that the locking pin 50 will enter the socket 52 in the assembled closed condition. The socket 52 includes a countersunk 54 in order to facilitate the entry of the locking pin 50 therein as the two sections 16, 18 are folded into their assembled closed condition.

With the two sections 16, 18 positioned in the opened condition as shown in FIG. 3, the sections are available for receiving the shank portion 12. The shank portion 12 includes a conventional flat section 56 at the rear thereof which will be received on the seat 48 of the section 18. The circumferential rib 42 of the section 16 will be received within a conventional annular groove 58 provided in the end portion of the tool shank 12. Thus, when inserted in the channels 40, 46, the tool shank 12 will rotate together with the overhandle 10, when the overhandle 10 is rotated, by means of the seat 48 engaging the flat section 56, and will be restrained from axial removal from the overhandle 10 by means of the circumferential rib 42 engaging in the annular groove 58.

Figure 2:
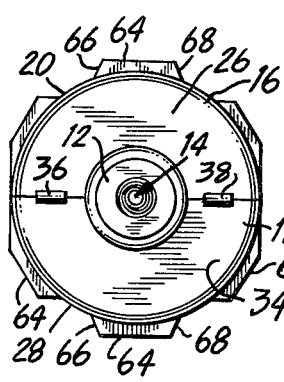
FIG. 2 is a front end view of the overhandle shown in FIG. 1.

When the two sections 16, 18 are to be folded over, the shank portion 12 is seated in one of the sections, and the forward ends 26, 34 are open so as to permit axial extension of the tool blade, as well as the shank portion, therethrough between the hinges 36, 38, as shown in FIGS. 1, 2 and 4. The two sections are folded over so that the locking pin 50 will tightly fit, such as a force-fit, within the socket 52, and the overhandle will be held in the assembled closed condition. In this way, the seat 48 engages the flat section 56 and the rib 42 engages in the groove 58, and the shank portion 12 will be securely held within the overhandle 10 so that the overhandle will convert the machine driven tool into a hand operated tool which can then be manually manipulated.

In order to facilitate the holding of the overhandle, grasping ribs are provided about the semi-cylindrical surfaces of the two sections. Specifically, the grasping ribs are formed of circumferential ribs or pads which are separated by axially spaced apart circumferential slots 60, and circumferentially spaced apart axial slots 62, in order to define an array of grasping pads or ribs 64 which appear as individual islands surrounded by the slots. The particular grasping pads have squared edges 66, 68 in order to permit easier manufacture thereof.

Referring now to FIGS. 5 and 6, a second embodiment of the present invention is shown and specifically for use in conjunction with a hand operated tool. The hand operated tool is shown at 70 and includes a handle 72 having an hourglass configuration and supporting a tool blade 74. The tool blade 74 can be a dental drill bit, file, reamer, etc. The handle 72 includes a head section 76, and a rear end section 78 interconnected by a narrowed midsection 79. Raised grasping ribs 81, 83 are formed on the midsection 79 and are axially spaced apart along a common plane. The ribs 81, 83 also are formed in circumferentially spaced apart relationship about the midsection 79 of the handle 72, as shown in FIGS. 5 and 6. An identification marking 85 is provided on the rear wall of the handle 72, as indicated in FIG. 5.

The overhandle is formed of two sections 80, 82. Each of the sections includes a similar arrangement as heretofore described in connection with the first embodiment and accordingly, only those portions that are different will be described in detail.

Specifically, section 80 includes a channel or recess 84 formed of substantially semi-cylindrical shape and having its forward section inwardly tapered at 86 as it extends through the forward end face 87. A correspondingly similar semi-cylindrical channel or recess 88 is formed in section 82 which likewise includes an inwardly tapered section 89 as it extends through the forward end face 90 of the section 82.

Inwardly directed ribs or pads 91, 92 are respectively formed at the midsections of the channels 84, 88 in order to provide the channels with a suitable configuration for receiving the hourglass shaped handle. Furthermore, the spaced apart pads 91, 92 provide axially extending grooves 93, 94 extending therebetween in order to receive the ribs 81, 83 of the handle 72 therein, so that rotation of the overhandle will cause the handle 72 to rotate therewith.

Here again, when the two sections 80, 82 are to be folded over, the handle 72 is seated in one of the sections, and the forward ends 87, 90 are open so as to permit axial extension of the blade 74 therethrough between the hinges 95, as indicated in FIG. 6. When assembled, the channels 84, 88 will form an inner chamber which can accommodate the hourglass shape of the handle 72 with the ribs 81, 83 being accommodated within the grooves 93, 94. The forward end faces 87, 90, particularly the tapered end sections 86, 89 thereof, will prevent axial extraction of the handle 72 from the overhandle. It will also snugly hold the forward tapered head section 76 of the handle in order to provide a tight fit of the handle within the overhandle when the locking pin 97 is tightly fitted within the countersunk socket 99. Although a completely cylindrical rear section could be provided as shown in connection with the first embodiment, an alternate type of rear end is shown in FIGS. 5 and 7. Specifically, the end sections 96, 98 each have a respective notch 100, 102 formed on opposite sides of the longitudinal axis of the overhandle. In this manner, when the two sections are folded and formed into their assembled closed position, the two rear end sections 96, 98 will be laterally offset so that the front face 104 of the end section 98 will be exposed by the notch 100 formed on the end of the end section 96. Similarly, the forward face 106 of end section 96 will be exposed by means of the notch 102 of the rear end section 98. The two exposed faces 104, 106, lie in a common plane and are available for receiving fingers thereon in order to separate the two end sections 96, 98, and thereby separate the two semi-cylindrical sections 80, 82 which form the overhandle itself.

It should be appreciated that the offset rear end shown in FIGS. 5 and 7 can similarly be utilized in conjunction with the other embodiments of the present invention.

Referring now to FIG. 8, there is shown a third embodiment of the present invention including channels so as to accommodate both types of handles and shanks described in connection with the first two embodiments. Specifically, there is shown in FIG. 8 the two semi-cylindrical sections 108, 110 connected together by the hinges 109. Section 108 includes a channel 112 formed of a first semi-cylindrical shape of a large diameter, with a pair of semi-cylindrical recesses 114, 116 of a small diameter axially extending from either end of the channel 112. Recess 116 extends through the forward end face 118 of the section 108. A flat section or seat 120 is formed at the rear end of the recess 114. Radially extending pads or ribs 122 providing grooves 123 therebetween, are disposed in the midsection of the channel 112.

A similar cavity is formed in section 110 and includes the larger semi-cylindrical channel 112 with the radially extending pads or ribs 122A therein which provide the axially extending grooves 123A therebetween. Axially extending from either end of the channel 112A is the recesses of smaller radius including the forward recess 116A which extends across the forward end face 118A and the rearwardly extending recess 114A. The circumferential rib 124 is provided in the recess 114A. Furthermore, a locking pin 50A is provided on the section 110, and a matching countersunk socket 52A is provided on the section 108 for removably receiving the locking pin 50A in the same manner as set forth above.

It should be appreciated, that the semi-cylindrical channels 112, 112A, including the pads or recesses 122, 122A with their respective grooves 123, 123A correspond to the shape of the channels 84, 88 shown in connection with the embodiment of FIGS. 5 and 6 in order to accommodate the handle 72 of the hand operated tool 70. Thus, the various structure and remarks made in connection with the embodiment of FIGS. 5 and 6 would also apply to the shape of the channels 112, 112A in FIG. 8, wherein the handle 72 is shown in phantom lines in channel 112A of the section 110.

Similarly, the shape of the recesses 114, 114A, as well as the recesses 116, 116A, with the corresponding flat seat 120 and the rib 124, correspond to the embodiment shown in connection with FIGS. 1–4 in order to receive the shank portion 12 of an engine driven tool 14. Therefore, all the structure and remarks made in connection with that configuration shown in FIGS. 1–4 would apply to the configuration of the recesses 114, 114A and 116, 116A shown in FIG. 8, wherein the shank portion 12 is shown in phantom lines in recesses 114, 116 of the section 108. It is noted that the shank portion 12 would extend freely across the channels 112, 112A.

It is therefore appreciated that in the embodiment shown in FIG. 8, the overhandle could be used with either the hand operated tool 70 or with the machine driven tool 14.

Figure 9:
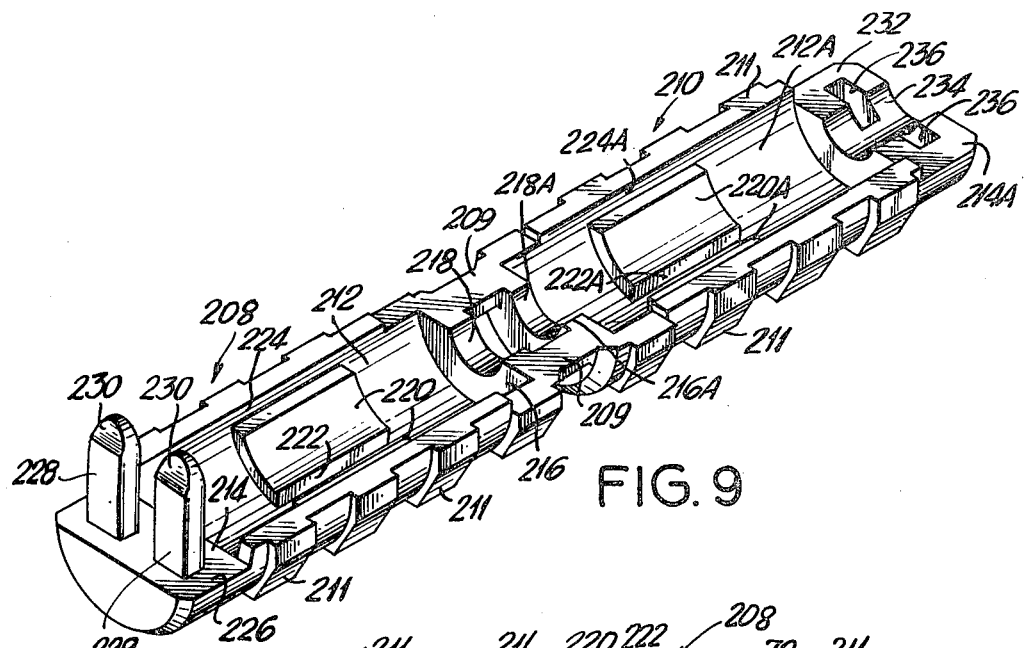
FIG. 9 is an exploded perspective view of an overhandle in accordance with a forth embodiment of the present invention in its opened condition.

Referring now to FIGS. 9–12, there is shown a fourth embodiment of the present invention including channels similar to those shown in FIG. 8 of the third embodiment so as to accommodate both types of handles and shanks previously described above. Specifically, there is shown in FIG. 9 the two semi-cylindrical sections 208, 210 connected together by the hinges 209. As in the other above embodiments, grasping ribs 211 are provided about the semi-cylindrical outer surfaces of the two sections, these ribs 211 being axially and circumferentially spaced apart in the same manner as set forth above to define an array of grasping pads or ribs which appear as individual islands surrounded by slots.

Section 208 includes a channel 212 having a semi-cylindrical shape disposed between a rear wall 214 and a forward wall 216. A semi-cylindrical recess 218 of a small diameter axially extends through the forward wall 216. A pair of radially extending pads or ribs 220 providing a groove 222 therebetween, is disposed in the midsection of the channel 212. The pads 220 are positioned a selected distance below the side edges of the section 208 to provide a space 224 therefrom at each side edge.

Section 210 includes a similar channel 212A having a semi-cylindrical shape disposed between a rear wall 214A and a forward wall 216A. A semi-cylindrical recess 218A of a small diameter axially extends through the forward wall 216A. A pair of radially extending pads or ribs 220A providing a groove 222A therebetween, is also disposed in the midsection of the channel 212A. The pads 220A are positioned a selected distance below the side edges of the section 210 to provide a space 224A therefrom at each side edge.

The rear wall 214 of section 208 includes a flat inner surface 226 stepped down from the side edges of the section 208 to provide a space therefrom. A pair of spaced apart prongs or tabs 228 extend perpendicularly upwardly from the flat surface 226. Each of the prongs 228 is provided with a tapered distal end 230, the function of which will be set forth below.

The rear wall 214A of section 210 also includes a flat surface 232 stepped down from the side edges of the section 210 to provide a space therefrom. A semi-cylindrical recess 234 of a small diameter axially extends through the rear wall 214A. A pair of spaced apart parallel openings 236 disposed at opposite sides of the recess 234 extends from the flat surface 232 through the rear wall 214A to the outer surface thereof.

Figure 10:
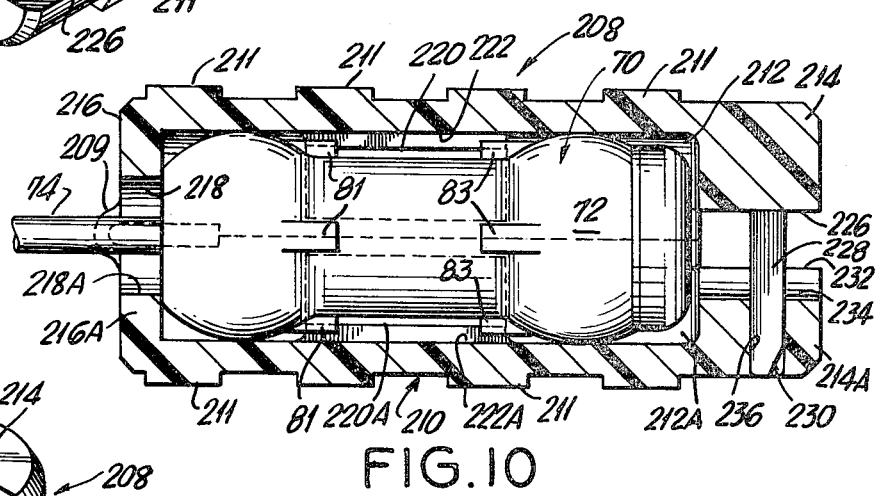
FIG. 10 is a side sectional view of the overhandle of FIG. 9 in an assembled closed condition enclosing the hand operated tool.
Figure 12:
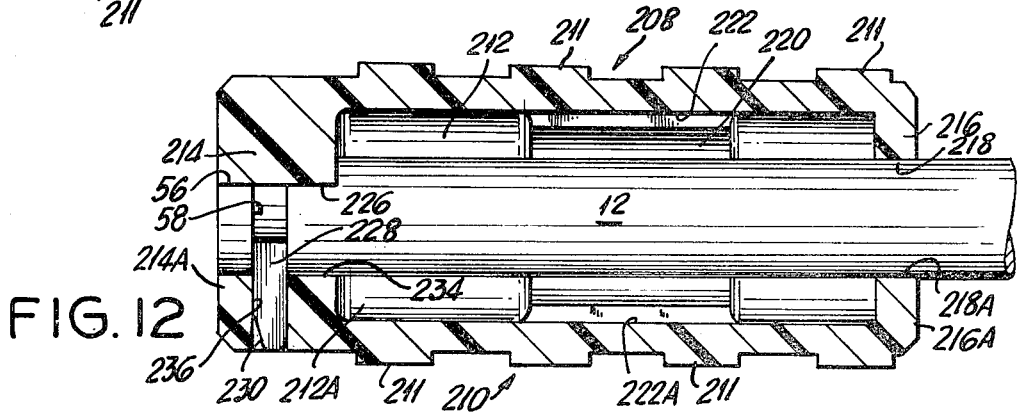
FIG. 12 is a side sectional view of the overhandle of FIG. 9 in an assembled closed condition enclosing the shank portion of an engine driven tool.

When the sections 208, 210 are closed together as shown in FIGS. 10 and 12, the prongs 228 of section 208 will be positioned in the parallel opening 236 of section 210 wherein the tapered ends 230 of the prongs 228 function to guide the prongs 228 into the openings 236 during the insertion thereof. The prongs 228 are held in the openings 236 perferably by a force fit engagement therebetween to secure the sections together.

Figure 11:
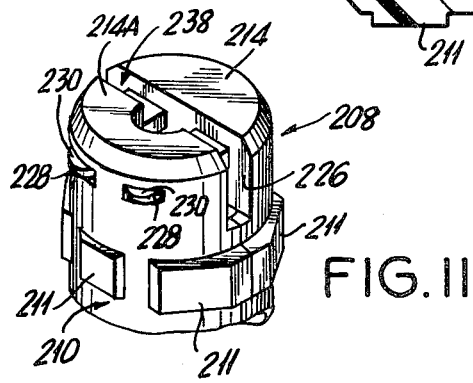
FIG. 11 is a fragmentary perspective end view showing the rear end of the overhandle of FIG. 9.

As set forth above, the flat surface 226 of the rear wall 214 of section 208 and the flat surface 232 of the rear wall 214A of section 210 are each spaced from the side edges of the sections 208, 210, so that when the two sections are folded into their assembled closed position with the side edges thereof abutting against each other, the flat surfaces 226, 232 will be spaced apart as shown in FIG. 11 to form a slot or notch 238 in the rear end of the instrument. Thus, the user of the instrument can insert his fingernails or other suitable tool into the slot 238 in order to separate the two sections 208, 210 when it is desired to remove the tool enclosed therein.

It should be appreciated, that the semi-cylindrical channels 212, 212A, including the pads 220, 220A with their respective grooves 222, 222A correspond to the shape of the channels 84, 88 shown in connection with the embodiment of FIGS. 5 and 6 in order to accommodate the handle 72 of the hand operated tool 70. Accordingly, the ribs 80, 83 of the tool 70 are locked in the grooves 222, 222A and in the grooves formed by the matching spaces 224, 224A of the sections 208, 210. Thus, the various structure and remarks made in connection with the embodiment of FIGS. 5 and 6 would also apply to the shape of the channels 212, 212A as best shown in FIG. 10 which shows the handle 72 enclosed in the instrument.

Similarly, the shape of the recess 234 of section 210 and the flat surface 226 of section 208 correspond to the recesses 40, 44 and flat seat 48 of the embodiment shown in connection with FIGS. 1-4 in order to receive the shank portion 12 of an engine driven tool 14, wherein the shank portion 12 extends freely across the channels 212 and 212A. However, the prongs 228 of section 208, in addition to securing the sections 208 and 210 together, also function to hold the shank portion 12 in place to prevent longitudinal axial movement thereof, and is therefore a modified version of the rib 42 shown in FIG. 3, performing the same function thereof. When the sections 208, 210 are folded and closed together, the prongs 228 are aligned to pass into the annular groove 58, on opposite sides of the shank portion 12, as indicated in FIG. 12, so that the shank portion 12 is enclosed in the instrument as shown. Therefore, the remarks made in connection with the configuration shown in FIGS. 1-4 would apply to the configuration shown in FIG. 12, where no further description thereof is thought necessary for a complete understanding of the present invention.

It is therefore appreciated that in the embodiment shown in FIGS. 9-12, the overhandle could be used for either the hand operated tool 70 or the machine driven tool 14, similar to the embodiment shown in FIG. 8.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. An overhandle for enclosing a cylindrical end portion of a rotatable dental tool, comprising:

two mating semi-cylindrical elongated first and second sections having respective first and second forward end faces, said forward end faces being confrontingly opposed to each other in an opened condition of said overhandle, and said forward end faces being in a single plane in an assembled closed condition of said overhandle with said sections disposed against each other to define an elongated cylindrical body capable of being rotated;

a pair of hinges interconnecting said forward end faces to provide a one piece construction and to permit said sections to pivot from said opened condition to said closed condition;

an elongated channel respectively provided in each of said sections to define first and second channels, each of said channels extending respectively through said first and second forward end faces, said channels being in axial alignment with each other in said opened condition, said channels matingly confronting each other in said assembled closed condition to define an internal chamber with a forward end having an opening therethrough, said chamber receiving the cylindrical end portion of the tool therein with a remaining portion of the tool axially extending through said chamber opening in said forward end;

said hinges being spaced apart with one of said hinges being disposed on one side of said chamber opening and the other hinge being disposed on an opposite side of said chamber opening to permit the remaining portion of the tool to extend between said hinges without any interference therefrom;

first means in at least one of said sections for preventing axial extraction of the end portion of the tool from said chamber;

second means in at least one of said sections for rotating the end portion of the tool when said overhandle is rotated;

releasable coupling means for retaining said sections together in said assembled closed condition to enclose the end portion of the tool therein and for permitting said sections to be pivoted into said opened condition to remove the end portion of the tool therefrom;

said sections having respective first and second rear end portions including rear end faces remote from said forward end faces to provide said overhandle with a rear end when in said assembled closed condition; and said coupling means including at least one locking member extending outwardly from said first rear end portion, and at least one recess located in a corresponding position in said second rear end portion for receiving said locking member in said assembled closed condition.

2. An overhandle as in claim 1 wherein said channels are semi-cylindrical in shape, and wherein said second means includes a seat at a remote end portion of said second channel for supporting a flat provided on the end of the tool, and said first means includes a circumferential rib adjacent a remote end portion of the first channel for engaging an annular groove provided in the end portion of the tool.

3. An overhandle as in claim 1, wherein the end portion of the tool has a handle thereon provided with ribs, said channels being substantially semi-cylindrical in shape, said second means including circumferentially disposed pads in said channels to support the handle in the chamber and to provide circumferentially spaced apart axially extending grooves between said pads for receiving the ribs provided on the handle.

4. An overhandle as in claim 3, wherein said first means includes said channels being inwardly tapered adjacent said forward end faces to thereby prevent axial removal of the enclosed handle.

5. An overhandle as in claim 1, wherein each of said channels includes a substantially semi-cylindrical first space of a large radius and semi-cylindrical second spaces of a small radius axially extending from both ends of said first space, and wherein said second means includes a seat at a remote end portion of one of said second spaces of said second channel for supporting a flat provided on the end portion of the tool, said first means including a circumferential rib adjacent a remote end portion of an associated one of said second spaces of the first channel for engaging an annular groove provided in the end portion of the tool, said second means further including circumferentially disposed pads in each said first space to support a handle disposed on an end of another tool and to provide circumferentially spaced apart axially extending grooves between said pads for receiving ribs provided on the handle of the other tool.

6. An overhandle as in claim 5, wherein each said first space is inwardly tapered adjacent said second spaces which extend to said forward end faces.

7. An overhandle as in claim 1, wherein said rear end portions of said sections are provided with notches on respective laterally opposite sides, said notches being laterally offset in said assembled closed condition to provide laterally spaced apart exposed surfaces along a common plane for facilitating opening of said overhandle from said closed condition to said open condition.

8. An overhandle as in claim 1, wherein said rear end portions of said sections are spaced apart in said closed condition to provide a slot therebetween for facilitating opening of said overhandle from said closed condition to said opened condition.

9. An overhandle as in claim 1, and further comprising grasping ribs provided about an exterior surface of each of said sections.

10. An overhandle as in claim 1, wherein said coupling means includes a pair of locking members defining prongs extending outwardly from said first rear end portion, and a pair of recesses defining transverse openings through the second rear end portion for receiving said prongs therein in said assembled closed condition.

11. An overhandle as in claim 10, wherein said prongs are spaced apart a selected distance for engaging therebetween an annular groove provided in the end portion of the tool to thereby define said first means for preventing axial extraction of the end portion from said chamber.

12. An overhandle as in claim 11, wherein said second rear end portion has a longitudinal recess therethrough for receiving said end portion of the tool, said first rear end portion providing a seat for supporting a flat provided on said end portion of the tool to thereby define said second means for preventing rotational movement between said overhandle and the tool.

13. An overhandle as in claim 12, wherein each of said channels includes a substantially semi-cylindrical space, said second means further including circumferentially disposed pads in each of said semi-cylindrical spaces to support a handle disposed on an end of another tool and to provide circumferentially spaced apart axially extending grooves between said pads for receiving ribs provided on the handle of the other tool.

14. An overhandle as in claim 10, wherein the end portion of the tool has a handle thereon provided with ribs, said channels being substantially semi-cylindrical in shape, said second means including circumferentially disposed pads in said channels to support the handle in the chamber and to provide circumferentially spaced apart axially extending grooves between said pads for receiving the ribs provided on the handle.

15. An overhandle as in claim 1, wherein said locking member is a pin and said recess is a socket.

* * * * *